United States Patent [19]

Sakiyama et al.

[11] Patent Number: 5,248,599
[45] Date of Patent: Sep. 28, 1993

[54] ACHROMOBACTER PROTEASE I GENE AND GENE PRODUCT THEREOF

[75] Inventors: Fumio Sakiyama, Suita; Atsuo Nakata, Toyonaka, both of Japan

[73] Assignee: Waco Pure Chemical Industries, Ltd., Osaka, Japan

[21] Appl. No.: 482,266

[22] Filed: Feb. 20, 1990

[30] Foreign Application Priority Data

Mar. 14, 1989 [JP] Japan .................................. 1-59726

[51] Int. Cl.$^5$ ...................... C12P 21/02; C12N 15/57; C12N 15/63; C12N 15/31
[52] U.S. Cl. ................... 435/69.1; 435/320.1; 435/220; 435/824; 536/23.2; 935/14
[58] Field of Search ................ 435/69.1, 71.1, 71.2, 435/220; 824/320.1; 935/9, 11, 72; 536/27, 23.2

[56] References Cited

U.S. PATENT DOCUMENTS 4,581,332  4/1986  Soejima et al. ...................... 435/220
4,624,926  11/1986  Inouye et al. ...................... 435/253

OTHER PUBLICATIONS

Young, R. A., et al. Proc. Nat'l Acad. Sci., USA. 80: 1194–1198 (1983).

Primary Examiner—Robert A. Wax
Assistant Examiner—G. E. Bugaisky
Attorney, Agent, or Firm—David G. Conlin; David S. Resnick

[57] ABSTRACT

Disclosed is a DNA sequence containing a DNA segment coding for Achromobacter protease I (API) or variants thereof (referred to as T-API); a recombinant DNA constructed by introducing the DNA sequence in an expression vector so as to express the T-API; a transformant bearing the recombinant DNA; a process for producing the API which comprises cultivating the transformant, accumulating the T-API in a culture product, and recovering the same: and a protein of T-API. The cells transfected or transformed with the DNA sequence of the present invention allow for the production of a large amount of precursor protein of the T-API or the mature peptide.

10 Claims, 9 Drawing Sheets

FIG. 1-1

```
5' GAATT CCG  CGC   GCG  TTC  TCA   ATT  TCG  TGT   TTT  CAT  CTG
                     9                 18          27           36         45    54

CAA  CAA   CTC   GTC  GTA  TGC   ACG  GTG  TGC   ACG  CAC  CGA
                     63                72          81           90         99   108
                    Leu                Val         Thr          Thr        His  Arg

GGG  ATT   TGC   TTC  TTG  TGC   CGG  GCG  TGC   GTG  AGC  CGC
                    117               126         135         144        153   162
                    Cys                Leu         Ala         Val         Ser  Arg

CAT  GCG   GCG   AAC  TTG  CAC   AAA  GCT  CGG   ATT  AGT  GCC
                    171               180         189         198        207   216
                    Ala                Leu         Arg         Ile         Ser  Ala

TCG  CTG   GCG   AGT  GCG  CAA   CGG  ACG  CGA   GTA  CGA  AAT
                    225               234         243         252        261   270
                    Ala                Ser         Arg         Val         Arg  Asn

CCG  CCT   TAC   CCT  AGC  CAT   CCC  CTT  CAC   ACC  GCA  GTT
                    279               288         297         306        315   324
                    Tyr                Leu         His         Thr         Ala  Val

CAT  CCA   GCA   CGG  CCA  CGG   GGC  CCT  TCG   GGC  TCA  CGG
                    333               342         351         360        369   378
                    Ala                Pro         Ser         Gly         His  Arg

CAA  GCA   ATG   AAA  CGC  TGT   GGT  CTG  CTG   CTC  GGT  ATC
   -205           387               396         405         414        423   432
                    Met                Arg         Cys         Gly         Leu  Ile
                    Lys                Ile         Ser         Leu         Gly  Ser

GCC  GCG   CTC   GCC  GCC  GCC   TCG  CCC  GCG   CCC  TTC  AAT
   -189          441               450         459         468        477   486
                    Leu                Ala         Ser         Ala         Phe  Asn
                    Ala                Pro         Arg         Ala         Tyr  Leu

TCC  AGC   GTC   GAC  AAG  GCC   GCC  TTG  CGC   ATG  GTC  AAG
   -171          495               504         513         522        531   540
                    Val                Asp         Lys         Met         Val  Lys
                    Ser                Val         Lys         Ala         Asp  Ala

Ser  Val   Asp   Ala  Thr  Leu   Arg  Pro
```

| Row start | Codons (nt position / codon / amino acid) |
|---|---|
| -153 | GCC Ala — AAG Lys — 549 GCC Ala — GAA Glu — GAT Asp — 558 TTG Leu — CAG Gln — CGC Arg — 567 GAC Asp — AAG Lys — CGC Arg — 576 GGC Gly — ATC Ile — CAG Gln — 585 CCG Pro — CGC Arg — TTC Phe — 594 GCC Ala |
| -135 | CTG Leu — GCG Ala — 603 ATC Ile — GAC Asp — GTG Val — 612 GAC Asp — ATG Met — ACC Thr — 621 CCT Pro — AAT Asn — CAG Gln — 630 TCC Ser — GCG Ala — AAC Asn — 639 TGG Trp — GAA Glu — TAC Tyr — 648 ACC Thr |
| -117 | GCC Ala — GAC Asp — 657 GGC Gly — CAG Gln — TTC Phe — 666 GCC Ala — GTA Val — TGG Trp — 675 CGC Arg — CAG Gln — CAG Gln — 684 GTT Val — GCG Ala — TCG Ser — 693 GAG Glu — AAG Lys — GCG Ala — 702 CTG Leu |
| -99 | TCA Ser — TTC AAC (Asn) — 711 AAC Asn — TTC Phe — TTC Phe — 720 GGT Gly — ACC Thr — GAC Asp — 729 TAC Tyr — ATG Met — TAC Tyr — 738 CCC Pro — GGC Gly — CGC Arg — 747 GGC Gly — GGC Gly — CTG Leu — 756 CTG Leu |
| -81 | GTA Val — TAT Tyr — 765 CCG Pro — GCG Ala — ACT Thr — 774 CAG Gln — GCG Ala — CCG Pro — 783 GCC Ala — GGC Gly — GAT Asp — 792 CGC Arg — GGC Gly — TTG Leu — 801 ATC Ile — AGC Ser — CAG Gln — 810 TAC Tyr |
| -63 | GAC Asp — GCC Ala — 819 AGC Ser — AAC Asn — AAC Asn — 828 AAC Asn — TCG Ser — GCG Ala — 837 CGC Arg — CTG Leu — TGG Trp — 846 TGG Trp — GCA Ala — GTG Val — 855 GTG Val — GTG Val — CCG Pro — 864 GGC Gly |
| -45 | GCC Ala — GAA Glu — 873 GCG Ala — ATC Ile — GAA Glu — 882 GCG Ala — GCG Ala — GTG Val — 891 ATC Ile — GAC Asp — CGC Arg — 900 GAC Asp — AAG Lys — GTC Val — 909 GGC Gly — GAG Glu — TTC Phe — 918 AAG Lys |
| -27 | CTG Leu — CGC Arg — 927 CTG Leu — ACC Thr — AAG Lys — 936 GTC Val — CAC His — GAC Asp — 945 GAC Asp — TAC Tyr — GTC Val — 954 GGT Gly — GGC Gly — TTC Phe — 963 CCG Pro — CTC Leu — GCG Ala — 972 CGC Arg |

FIG. 1-3

| Res. | | | | | | | | | | | | | | | | | | |
|---|---|---|---|---|---|---|---|---|---|---|---|---|---|---|---|---|---|---|
| −9 | CGC Arg | CTG Leu | 981 GCC Ala | GCT Ala | 990 TCC Ser | GCG Ala | 999 GAG Glu | AAG Lys | GGC Gly | 1008 GTG Val | TCG Ser | 1017 TGC Cys | TCG Ser | GGT Gly | 1026 GAC Asp | ATC Ile | AAC Asn | |
| 10 | GTG Val | GTC Val | 1035 TGC Cys | CCC Pro | 1044 GGC Gly | GAA Gly | 1053 CGC Arg +1 | GGC Gly | CGC Arg | 1062 GAC Asp | ATC Ile | 1071 GCG Ala | CGC Arg | ATC Ile | 1080 GCG Ala | GGT Gly | GTC Val | |
| 28 | TAC Tyr | TCG Ser | 1089 AAG Lys | AGC Ser | 1098 ACG Thr | GGC Gly | 1107 TGT Cys | GCC Ala | ACC Thr | 1116 GGT Gly | CTG Leu | 1125 AAC Asn | GTC Val | CTG Leu | 1134 GCC Ala | ACC Thr | AAC Asn | |
| 46 | AAC Asn | GAC Asp | 1143 CGC Arg | AAG Lys | 1152 TAC Tyr | ATG Met | 1161 ACC Thr | CTG Leu | GCG Ala | 1170 CAC His | CAC His | 1179 ATG Met | GGC Gly | TGC Cys | 1188 GCC Ala | ACG Thr | GGC Gly | |
| 64 | TCG Ser | ACC Thr | 1197 GCC Ala | GCG Ala | 1206 ATC Ile | TCG Ser | 1215 TAC Tyr | GTG Val | TGG Trp | 1224 AAC Asn | TAT Tyr | 1233 TCG Ser | CAG Gln | CAG Gln | 1242 CGC Arg | TGC Cys | ACC Thr | |
| 82 | GCG Ala | CCC Pro | 1251 AAC Asn | ACG Thr | 1260 GCC Ala | CCG Pro | 1269 GCC Ala | TGG Trp | AAC Asn | 1278 GGC Gly | GAC Asp | 1287 ATG Met | GGC Gly | TCC Ser | 1296 ACC Thr | CAG Gln | AGC Ser | |
| 100 | CAG Gln | TCG Ser | 1305 GGT Gly | TCG Ser | 1314 GTC Val | ACG Thr | 1323 ACC Thr | TAC Tyr | TAC Tyr | 1332 GCC Ala | ACC Thr | 1341 TTC Phe | GAC Asp | TTC Phe | 1350 CTC Leu | CTG Leu | ACC Thr | |
| 118 | GAG Glu | TTG Leu | 1359 AAC Asn | AAT Asn | 1368 GCC Ala | GCG Ala | 1377 GCG Ala | TTC Phe | TTC Phe | 1386 AAC Asn | CTG Leu | 1395 GCC Ala | TGG Trp | TTC Phe | 1404 GAC Asp | TGG Trp | GGT Gly | |
| 136 | CGT Arg | CGC Arg | 1413 GAC Asp | CAG Gln | 1422 TAT Tyr | AAC Asn | 1431 GCG Ala | ATC Ile | ATC Ile | 1440 ATC Ile | CCC Pro | 1449 CCC Pro | CAT His | CAC His | 1458 GCC Ala | GTC Val | AAC Asn | |

| | | | | | | | | | 1512 GGC Gly |
|---|---|---|---|---|---|---|---|---|---|
| 154 | GAG Glu | AAG Lys | 1467 CGC Arg | ATC Ile | AGC Ser | 1476 AAC Asn | TCC Ser | ACC Thr | 1485 AGC Ser | CCG Pro | ACC Thr | TTC Phe | GTG Val | 1503 GCC Ala | TGG Trp | GGC Gly |
| 172 | GGC Gly | GCC Ala | 1521 GGC Gly | ACC Thr | ACG Thr | 1530 CAT His | TTG Leu | AAC Asn | 1539 GTG Val | CAG Gln | CCC Pro | TCG Ser | 1557 GGC Gly | GGC Gly | GTG Val | 1566 ACC Thr |
| 190 | GAG Glu | CCG Pro | 1575 GGT Gly | TCG Ser | TCG Ser | 1584 GGT Gly | TCG Ser | CCG Pro | 1593 ATC Ile | TAC Tyr | AGC Ser | GAA Glu | AAG Lys | 1611 CGC Arg | GTG Val | CTC Leu |
| 208 | CAG Gln | CTG Leu | 1629 CAC His | GGC Gly | GGC Gly | 1638 CCG Pro | TCG Ser | AGC Ser | 1647 TGC Cys | AGC Ser | AGC Ser | GGC Gly | ACC Thr | 1665 CGC Arg | GCC Ala | AGC Ser | 1674 GAC Asp |
| 226 | CAG Gln | TAC Tyr | 1683 GGC Gly | CGC Arg | GTG Val | 1692 TTC Phe | AAC Asn | TAC Tyr | 1701 TGG Trp | ACC Thr | AGC Ser | GGC Gly | GGC Gly | 1719 GCC Ala | GCC Ala | TCG Ser | 1728 CGC Arg |
| 244 | CTG Leu | AGC Ser | 1737 GAT Asp | TGG Trp | CTC Leu | 1746 GAT Asp | CCG Pro | GCC Ala | 1755 AGC Ser | CCG Pro | GGC Gly | CAG Gln | TTC Phe | 1773 ATC Ile | CGC Arg | GGC Gly | 1782 CTG Leu |
| 262 | GAT Asp | TCG Ser | 1791 GGC Gly | GGC Gly | GGC Gly | 1800 ACG Thr | CCG Pro | AAC Asn | 1809 ACT Thr | CCG Pro | CCG Pro | GCG Ala | AAC Asn | 1827 TTC Phe | GAC Asp | TCC Ser | 1836 ACC Thr |
| 280 | ACC Thr | AGC Ser | 1845 GGC Gly | CTG Leu | ACC Thr | 1854 GCG Ala | ACC Thr | TTC Phe | 1863 ACC Thr | GAC Asp | AGC Ser | ACC Thr | GAC Asp | 1881 AGC Ser | GAC Asp | GGT Gly | 1890 TCG Ser |
| 298 | ATC Ile | GCC Ala | 1899 TCG Ser | CGT Arg | AGC Ser | 1908 TGG Trp | AAC Asn | TTC Phe | 1917 GGC Gly | GAC Asp | AGC Ser | ACC Thr | TCG Ser | 1935 ACC Thr | GCG Ala | AAC Asn | 1944 ACC Thr |

| AA pos | 1 | 2 | 3 | 4 | 5 | 6 | 7 | 8 | 9 | 10 | 11 | 12 | 13 | 14 | 15 | 16 | 17 | 18 |
|---|---|---|---|---|---|---|---|---|---|---|---|---|---|---|---|---|---|---|
| 316 | CCG Pro | AGC Ser | 1953 AAG Lys | ACC Thr | TAC Tyr | 1962 GCC Ala | ACC Thr | GCG Ala | 1971 GGC Gly | ACC Thr | TAC Tyr | 1980 GTC Val | ACC Thr | ACG Thr | 1989 GTC Val | CTG Leu | ACG Thr | 1998 ACC Thr |
| 334 | GAC Asp | AAC Asn | GGC Gly | ACC Thr | GCC Ala | 2007 ACC Thr | AAC Asn | AAG Lys | 2016 ACC Thr | ACC Thr | TCG Ser | 2025 GTC Val | GGT Gly | ACC Thr | 2034 GTG Val | ACC Thr | TCC Ser | 2043 GGC Gly |
| 352 | CCG Pro | GGT Gly | GCG Ala | CAG Gln | ACC Thr | GAC Asp | TAC Tyr | GAT Asp | GTG Val | ACC Thr | AAC Asn | GCG Ala | GAT Asp | ATC Ile | CCG Pro | GAC Asp | AAC Asn | AAC Asn |
| 370 | ACG Thr | GTC Val | AGC Ser | CAG Gln | ATC Ile | AAC Asn | ACC Thr | CGC Arg | TCC Ser | CGC Arg | GTG Val | GCG Ala | TCG Ser | GGC Gly | Ala |  |  |  |
| 388 | ACG Thr | CCG Pro | Ile | CAG Gln | Thr | GTG Val | Val | AGC Ser | Asp | TAC Tyr | AAG Lys | Asp | GAT Asp | GTG Val |  |  |  |  |
| 406 | CTG Leu | GTC Val | GCG Ala | CCG Pro | ACC Thr | GTC Val | CAC His | TAC Tyr | CTG Leu | AAC Asn | CAC His | CGC Arg | ACC Thr | GGC Gly | Gly |  |  |  |
| 424 | GCG Ala | CAC His | AAC Asn | ATC Ile | Ile | ACC Thr | TAC Tyr | TTC Phe | AAG Lys | GAC Asp | CTG Leu | AGC Ser | GAA Glu | Glu | GCT Ala | Ala |  |  |
| 442 | CGG Arg | GCA Ala | CCT Pro | AGC Ser | ACG Thr | GGG Gly | TGA *** | ACG Thr | ACA Thr | ACG Thr | CCA |  | CCG |  | CCC |  | GCA | GCC |
|  | TCG | ACA | AGT | GGA | GCA | TCA | GCA | CGC | TTC | TGA | TGC | CCA | TGG |  |  |  |  | 2414 3' |

5,248,599

ACHROMOBACTER PROTEASE I GENE AND GENE PRODUCT THEREOF

BACKGROUND OF THE INVENTION

The present invention relates to cloning a DNA coding for Achromobacter protease I (API) or variants thereof having similar activity to API, and further relates to the production of API or variants thereof using the cloned DNA segment.

API is a serine protease which was isolated from *Achromobacter lyticus* M497-1. API specifically cleaves the peptide bonds (—Lys—X—) at the side of the carboxyl groups of lysine residues in proteins and peptides, and is also called a lysyl end peptidase (EC 3.4.21.50). This enzyme cleaves all Lys—X bonds including the Lys—Pro bond, and therefore is very useful for the fragmentation of proteins or peptides for their primary structural analysis, in the preparation of peptide maps or in the synthesis of —Lys—X— components.

On the other hand, the isolation and purification of proteins and polypeptides secreted by certain kinds of cells is usually very difficult, because, for example, the small amount of protein secreted. In order to solve this problem, recombinant DNA techniques have recently been employed.

The production of API has relied on the isolation of the native protein from *Achromobacter lyticus*. However, this natural API is isolated in very small amounts, so that there has been a desire in the art to develop a process for producing API in large amounts.

SUMMARY OF THE INVENTION

In order to provide a process for producing Achromobacter protease I (API) or variants thereof having similar activity to API (hereinafter they are referred as T-API) by recombinant DNA techniques, the present inventors have studied, and consequently have succeeded in producing T-API by cloning a DNA segment for coding for the T-API and using the cloned T-API. In accordance with the present invention, there are provided (1) a DNA sequence containing a DNA segment coding for a T-API, (2) a recombinant DNA constructed by introducing the DNA sequence in an expression vector so as to express a T-API, (3) a transformant bearing the recombinant DNA, (4) a process for producing a T-API which comprises cultivating the transformant under conditions suitable for the expression of the T-API in the culture, and recovering the same, and (5) a T-API protein.

BRIEF DESCRIPTION OF THE DRAWINGS

FIG. 1(1)–1(5) show a DNA sequence containing a DNA segment coding for a T-API, and the deduced amino acid sequence corresponding thereto;

DESCRIPTION OF THE PREFERRED EMBODIMENTS

Figure 2:
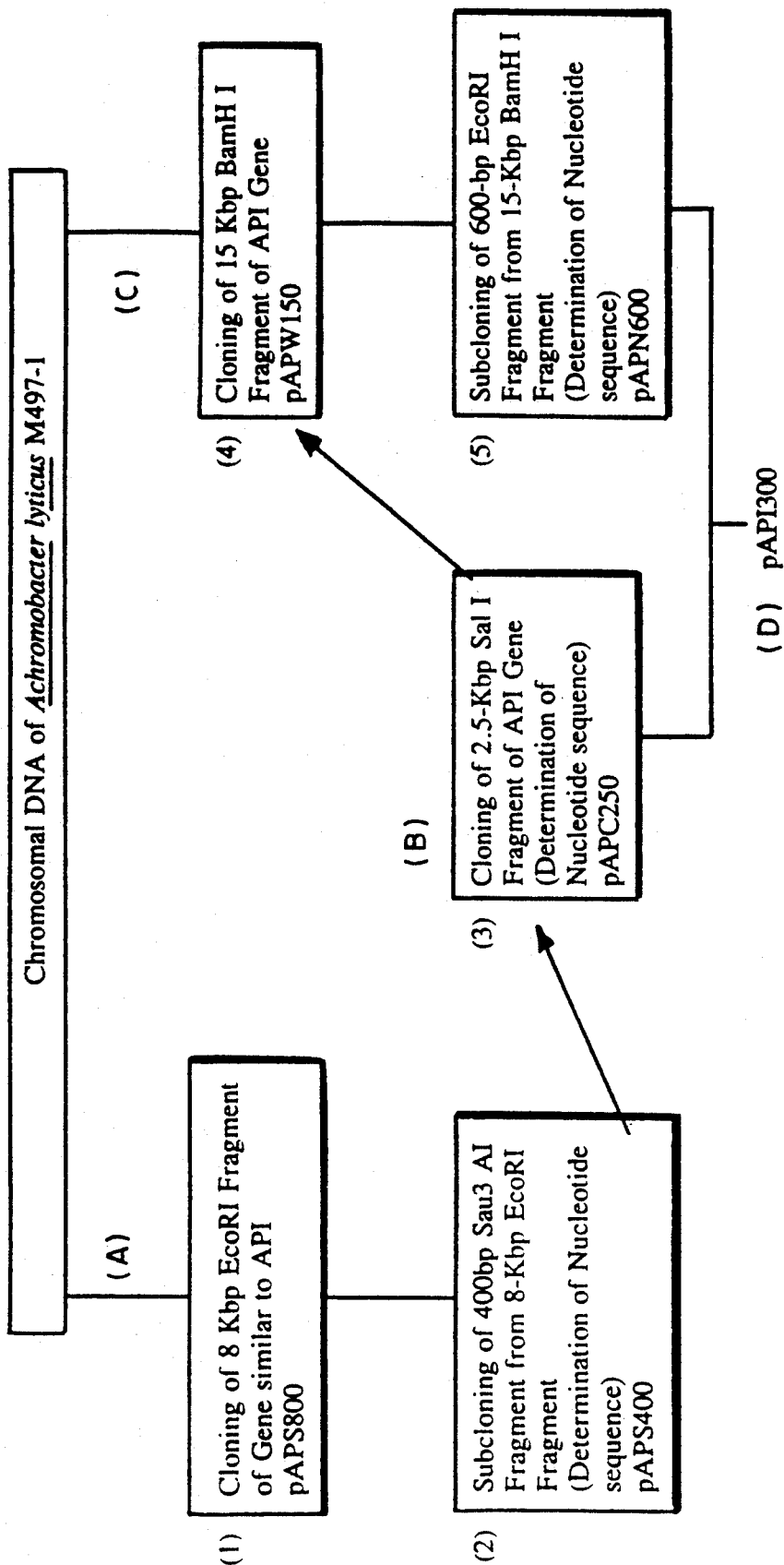
FIG. 2 is a flowchart showing the course of the cloning of the DNA segment coding for the T-API of the present invention.

In cloning a T-API gene, the present inventors obtained a gene having the DNA sequence extending from position 1 to position 2414 shown in FIG. 1. In this sequence, positions 387 to 2348 are expressed as a protein (prepro form), positions 387 to 449 (or 387 to 470) encode a signal sequence and positions 1002 to 1805 encode a mature protein. The region located at positions 1002 to 2348 can be called a mature protein encoding region since the protein encoded by this region has activity similar to that of the mature protein encoded by the region located at position 1002 to 1805. In the construction of a T-API expression system, a nucleotide sequence extending from position 354 to position 2414 is introduced. However, a sequence included in this nucleotide sequence is shorter than this sequence can be used as long as it can express a T-API.

An amino acid sequence deduced from this DNA sequence is also shown in FIG. 1. In this amino acid sequence, positions 1 to 268 correspond to the mature protein region, positions 1 to 269 or to 448 correspond to the mature protein region in a wide sense as having activity similar to that of the mature protein region extending from position 1 to position 268, and positions 205 to 448 correspond to the protein expression region (prepro form).

In this invention, a T-API gene is a general term for genes encoding the mature protein region (API) extending from position 1 to position 268 in the amino acid sequence or the mature protein region in a wide sense as having activity similar to that of the mature protein region extending from position 1 to position 268 and corresponding to positions 1 to 269 or up to 448.

In the present invention, for example, an expression vector having the DNA sequence containing the nucleotide sequence coding for a T-API can be prepared by the following process:

(a) Whole genomic DNA separated from API-producing cells such as *Achromobacter lyticus* M497-1 is digested with a restriction enzyme.
(b) DNA restriction fragments are introduced into a phage or a plasmid.
(c) A host cell is transformed with the recombinant phage or plasmid thus obtained.
(d) After cultivation of the transformant thus obtained, the plasmid or phage containing the desired DNA sequence is isolated from the transformant by an appropriate method such as hybridization with a DNA probe coding for a portion of a T-API.
(e) The desired cloned DNA sequence is cut out from the recombinant DNA.
(f) The cloned DNA sequence or a portion thereof is ligated downstream from a promoter in the expression vector.

The DNA segment coding for a T-API can also be prepared fully synthetically or semi-synthetically. In this case, the DNA segment can be synthesized, based on the sequence shown in FIG. 1.

When the whole genomic DNA of a T-API is digested with a restriction enzyme, there are used restriction enzymes such as EcoRI, SalI and BamHI.

Examples of the plasmids into which the digested DNA fragment is introduced include pACYC177, pACYC184, pUC8. pUC9, pBR322, pIN3A1 and pKK233-2, each derived from *Escherichia coli*. However, any other plasmid can be used as long as it is able to replicate in the host cell.

The phage vectors into which the DNA fragment is introduced include, for example. M13 phage mp9, M13 phage mp8. gt11, EMBL3 and Charon 4. However, any other phage vector can be used as long as it is able to grow in the host cell The plasmid thus obtained is introduced into the appropriate host cells such as Escherichia (*Escherichia coli*). Bacillus (*Bacillus subtilis*), Streptomyces (actinomycetes), Saccharomyces (yeast) and monkey COS cell, an animal cell.

Examples of Escherichia described above include *Escherichia coli* UT481, JM103, JM83, JM109, NM522 and MV1304. Examples of Bacillus described above include *Bacillus subtilis*. Examples of Streptomyces coelicolor. Examples of Saccharomyces include *Saccharomyces cerevisiae*.

The phage vector or the plasmid containing the desired DNA is located from the transformant thus obtained, for example, by hybridization such as colony hybridization using an oligonucleotide coding for a portion of a T-API as a probe or plaque hybridization The outline of the cloning of a T-API gene or the present invention is shown in the flowchart of FIG. 2. An exact region coding for the T-API gene is determined through the course of [A] the cloning of DNA fragments having a sequence similar to that of the T-API gene and the determination of the nucleotide sequence of the cloned DNA sequence [(1)→(2)], [B] the cloning of the T-API gene and the determination of the nucleotide sequence of the cloned gene (3), [C] the cloning of the 5'-region of the T-API gene and the determination of the nucleotide sequence [(4)→(5)], and [D] the construction of the whole T-API gene.

The nucleotide sequence of the thus cloned DNA for coding the T-API is determined by use of a suitable restriction site if it exists, or by applying the dideoxy method with M13 phage to a deletion body prepared by using DNase I if the restriction site does not exist. The nucleotide sequence of the DNA as determined by the dideoxy method and the amino acid sequence deduced from that nucleotide sequence are shown in FIG. 1.

The DNA sequence coding for the T-API cloned as described above can be used as it is, or depending on its intended use after digestion with a restriction enzyme if desired The region intended to be expressed is cut out from the cloned DNA and ligated downstream from a promoter in a vector suitable for expression, whereby the expression vector can be obtained.

The DNA sequence has ATG as a translation initiating codon at the 5'-terminus thereof and may have TAA, TGA or TAG as a translation terminating codon at the 3'-terminus. These translation initiating codon and translation terminating codon may be added by use of an appropriate synthetic DNA adaptor. Further, in order to express the DNA sequence, a promoter is ligated upstream from the sequence.

Examples of the vectors include plasmids derived from Escherichia such as pACYC184, pUC9, pKK233-2, pACYC177, pUC8, pBR322 and pIN3AI, plasmid pHY300PLK derived from Bacillus, plasmids pBTI-1 and pMAC561 derived from Saccharomyces, plasmid PIJ61 derived from Streptomyces and plasmid pSVL derived from monkey COS cell.

As the promoter used in the present invention, any promoter is available as long as the promoter is suitable for expression corresponding to the host cell used for the gene expression When the host cell used for the translation is Escherichia, examples of the promoters include lac, tac, trp, lpp and phoS. When the host cell is Bacillus, examples of the promoters include SPO2 and α-amylase. When the host cell is Saccharomyces, examples of the promoters include $P_{ACDI}$ (alcohol dehydrogenase promoter) and $P_{CYCI}$ (cytochrome C promoter). In the case of the monkey COS cell, examples of the promoters include SV40 early and late promoters.

By using the vector containing the DNA sequence coding for the T-API thus constructed, a transformant can be formed.

The host cells include, for example, Escherichia, Bacillus, Streptomyces, Saccharomyces and monkey COS cell.

As illustrative examples of Escherichia, Bacillus, Streptomyces, Saccharomyces and monkey COS cell described above, there can be mentioned the same strains as described above.

Thus, the transformants transformed with the expression vector containing the DNA sequence coding for the T-API are obtained.

When the transformants are cultivated in the present invention, ordinary media may be used. Examples of the media include LB medium, M9 medium and T medium.

The pH of the medium is about 6 to 9. preferable about 7.

The cultivation time, the cultivation temperature and the cultivation method can be suitably selected However, shake cultures are preferable, and the cultivation temperature is preferable about 25° C., more preferably a slightly less than 25° C. The combination of a temperature of 25° C., a cultivation time of 24 hours and shake cultures in LB medium (pH 7.2) containing 1 mM of IPTG is particularly preferred.

The separation and purification of the T-API from the culture described above can be performed, for example, by the following method When the T-API is extracted from the cultivated cells, the cells are collected by a known method after the cultivation. Then, the collected cells are suspended in an appropriate buffer and disrupted by ultrasonic treatment, osmotic shock, lysozyme and/or freeze thawing. Thereafter, a crude extracted solution of the precursor protein of the T-API or the mature peptide is obtained by centrifugation or filtration. The buffer may contained a protein denaturant such as urea or guanidine hydrochloride, or a detergent such as Triton X-100.

When the precursor protein or the mature peptide is secreted in the culture, a supernatant is separated from the cells by a known method per se after the conclusion of cultivation, and then collected.

The separation and purification of the precursor protein or the mature peptide contained in the culture supernatant or the extracts thus obtained can be performed by an appropriate combination of known separating and purifying methods per se. These known separating and purifying methods include utilizing solubility such as salt precipitation and solvent precipitation, methods mainly utilizing a difference in molecular weight such as dialysis, ultrafiltration gel filtration and SDS-polyacrylamide gel electrophoresis, methods utilizing a difference in electric charge such as ion-exchange chromatography, methods utilizing specific affinity such as affinity chromatography, methods utilizing a difference in hydrophobicity such as reverse-phase high performance liquid chromatography and methods utilizing a difference in isoelectric point such as isoelectric-focusing electrophoresis.

The cells transfected or transformed with the DNA of the present invention allow a large amount of the precursor protein of a T-API or the mature peptide to be produced.

As described above. T-API is an enzyme which specifically cleaves the peptide bonds (—Lys—X—) on the side of the carboxyl groups of lysine residues in proteins and peptides and cleaves all Lys—X bonds including the Lys—Pro bond. T-API is therefore very useful for the fragmentation of the proteins or the peptides for their primary structural analysis, the preparation of peptide maps or the synthesis of —Lys—X— compounds.

When nucleotides, amino acids and so on are indicated by the abbreviations in this specification and drawings, the abbreviations adopted by IUPAC-IUB Commission on Biochemical Nomenclature or commonly used in the art are employed. For example, the following abbreviations are used. When optical isomers are capable for existing with respect to the amino acid, an L-form is represented unless otherwise specified.

DNA: Deoxyribonucleic acid
cDNA: Complementary deoxyribonucleic acid
A: Adenine
T: Thymine
G: Guanine
C: Cytosine
I: Inosine
RNA: Ribonucleic acid
mRNA: Messenger ribonucleic acid
dATP: Deoxyadenosine triphosphate
dTTP: Deoxythymidine triphosphate
dGTP: Deoxyguanosine triphosphate
dCTP: Deoxycytidine triphosphate
ATP: Adenosine triphosphate
Gly or G: Glycine
Ala or A: Alanine
Val or V: Valine
Leu or L: Leucine
Ile or I: Isoleucine
Ser or S: Serine
Thr or T: Threonine
Cys or C: Cysteine
Met or M: Methionine
Glu or E: Glutamic acid
Asp or D: Aspartic acid
Lys or K: Lysine
His or H: Histidine
Phe or F: Phenylalanine
Tyr or Y: Tyrosine
Trp or W: Tryptophan
Pro or P: Proline
Asn or N: Asparagine
Gln or Q: Glutamine With respect to a T-API of the present invention, a portion of the amino acid sequence may be modified, namely there may be addition, elimination or substitution with other amino acids as long as the activity is not lost.

The present invention will hereinafter be described in detail with the following Examples. It is understood of course that the Examples are not intended to limit the scope of the invention.

Materials and operations used in the following Examples are as follows:

(a) As restriction enzyme, modifying enzymes and a nucleotide sequence determination kit, products manufactured by Takara Shuzo were used. As DNase I, a product manufactured by Sigma was used. As DNA polymerase I, a product manufactured by New England Biolabs was used. As a nitrocellulose membrane. BA85 manufactured by Schleicher & Schuell was used. As a $^{32}P$ radioactive nucleotide. a product manufactured by Amersham Radiochemicals was used.

(b) An NcoI linker and a pKK233-2 vector used for expression were products manufactured by P L. Biochemicals. The genotypes of *Escherichia coli* strains used in this experiment are as follows:
UT481 lon Δ(lac, pro) thy A met sup D r m/F'traD36 proAB lacI$^q$ Z M15
JM103 Δ(lac, pro) thi strA supE endA sbcB15 hsdR4/f' traD36 proAB lacI$^q$ Z M15

(c) For labeling, 15 pmol of an oligonucleotide mixture was labeled with 100 μCi of [γ-$^{32}$P]ATP (>5000 Ci/mmol) by using T4 polynucleotide kinase. 0.5 to 1 μg of DNA fragments was labeled with 50 μCi of [α-$^{32}$P]dCTP (>3000 Ci/mmol) by nick translation.

(d) Hybridization

In colony hybridization, plaque hybridization and Southern hybridization, DNA transferred onto a nitrocellulose membrane was hybridized with a probe in the following manner:

When an oliqonucleotide was used

The membrane was maintained at 42° C. for 1 hour in a solution containing 5× Denhardt's solution, 0.1% SDS, 10% sodium dextran sulfate, 19.8 mM Tris HCl (pH 8.0). 6.0 mM EDTA and 0.9 M NaCl. Then, the labeled probe was added to the same solution, and the resulting solution was maintained at room temperature for 24 hours. The membrane was washed with 6×SSC at room temperature for 30 minutes 3 times and further at 40° C. for 5 minutes. Thereafter, autoradiography was conducted in the presence of an intensifier at −80° C. for 24 hours.

When a DNA fragment labeled by nick translation was used

The membrane was maintained at 42° C. for 2 hours in a solution containing 5×SSC, 50% formamide, 5×Denhardt's solution, 50 mM sodium phosphate buffer (pH 6.5) and 1 mg/ml of salmon sperm DNA treated with ultrasonication, and then transferred into a solution containing 5×SSC, 50% formamide, 1×Denhardt's solution, 10% sodium dextran sulfate, 20 mM sodium phosphate buffer and 1 mg/ml of salmon sperm DNA treated with ultrasonication, followed by addition of the labeled probe. The resulting solution was maintained at 42° C. for 24 hours. The membrane was washed with a solution of 2×SSC and 0.1% SDS at room temperature for 30 minutes 3 times, and further with a solution of 0.1×SSC and 0.11% SDS at 55° C. for 30 minutes 3 times.

Autoradiography was carried out in the same manner as described above.

(e) Screening was carried out in the following manner:

When whole qenomic DNA was used

250 μg of chromosomal DNA was digested with a restriction enzyme, and the resulting fragments were inserted into plasmids and used to obtain transformants.

Colony hybridization was performed using the transformants as a genomic DNA library.

When subcloning was carried out from a DNA fragment

20 μg of DNA fragments were digested with a restriction enzyme, and the resulting fragments were inserted into a plasmid or phage DNA and used to obtain transformants. Colony hybridization or plaque hybridization was conducted using the transformants as a DNA library.

When size-selected DNA was used

250 μg of chromosomal DNA was digested with a restriction enzyme, and subjected to 0.8% agarose gel electrophoresis. To the resulting DNA fragments, Southern hybridization was performed, and a region corresponding to a positive band was cut out from a gel similarly electrophoresed, followed by elution of the DNA fragments therefrom. The eluted DNA fragments were inserted into a plasmid and used to obtain transformants. Colony hybridization was carried out using the transformants thus obtained as a DNA library.

(f) Determination of DNA Nucleotide Sequence

The nucleotide sequence of the thus cloned DNA segment was determined by use of a suitable restriction site if it exists, or by applying the dideoxy method with M13 phage to a deletion body prepared by DNase I if the restriction site does not exist.

The gene manipulation methods described above were carried out in accordance with T. Maniatis, et al., *Molecular Cloning: A Laboratory Manual*, Cold Spring Harbor Laboratory, N.Y.

EXAMPLE 1 (REFER TO FIG. 2)

[A] Cloning of DNA Fragments Having Sequence Similar to That of API Gene and Determination of Its Nucleotide Sequence (1) Cloning of API-like Gene 8-Kbp EcoRI Fragment 250 μg of genomic DNA obtained from *Achromobacter lyticus* M497-1 was digested with EcoRI, and the resulting fragments were inserted into pACYC184 and used to obtain transformants. Approximately 6,000 of the transformants were screened by colony hybridization using the oligonucleotide set out below as a probe. The probe was obtained by labeling the 5'-terminus of the following 21-mer synthesized based on the primary structure (coding for the amino acid sequence located at positions 71 to 77 of the mature protein) of the API protein, by using T₄ polynucleotide kinase:

This probe was specific to the API gene. After washing at room temperature, autoradiography was carried out and colony hybridization was performed for about 600 replica clones, followed by washing at 42° C. An autoradiogram located one positive clone, which contained an 8-Kbp fragment (pAS800). The about 8-Kbp EcoRI fragment was recovered.

(2) Subcloning of 400-bp Sau3AI fragment in 8 Kbp EcoRI Fragment and Determination of Nucleotide Sequence Thereof The 8-Kbp EcoRI fragment was digested with Sau3AI, and the resulting fragment was inserted into M13 phage mp9 to obtain transformed plaques. About 1,000 of the transformed plaques thus obtained were screened by plaque hybridization using the above oligonucleotide as a probe. Autoradiography after washing at 42° C. found 13 clones were positive. For these clones, the nucleotide sequence was determined by the dideoxy method and the amino acid sequence deduced. This proved that the cloned DNA fragments had a homology of about 70% with API at the amino acid level. Then, this fragment was cut out from mp9 by EcoRI/HindIII digestion and transferred to pUC9 (pAPS400).

[B] Cloning of API Gene and Determination of Its Nucleotide Sequence (3) Cloning of API Gene 2.5-Kbp SalI Fragment 1 μg of the about 400-bp fragments obtained by EcoRI/PstI digestion of pAPS400 obtained in (2) was labeled by nick translation [α-³²P]dCTP to prepare a probe. 250 μg of whole genomic *Achromobacter lyticus* M497-1 DNA was digested with SalI, and Southern hybridization was performed using the above probe. Although two bands were observed on the autoradiograms, the intense one was considered to correspond to the DNA having a similar sequence previously cloned. Accordingly, a region corresponding to the 2.5 Kbp weak band was cut out from a gel similarly electrophoresed to collect DNA fragments. The resulting DNA fragments were inserted into pUC9 and used to obtain transformants. Using about 2,000 of the transformants thus obtained as a library, screening was carried out by colony hybridization using the above 400-bp DNA fragment as a probe. 12 positive clones were obtained. Plasmids were prepared from each colony, and SalI digestion thereof was carried out Then, it was confirmed by Southern hybridization of the same probe to be the desired about 2.5-Kbp fragments (pAPC250). This 2.5-Kbp fragment was cut out with SalI and collected, followed by insertion into the SalI site of M13 phage mp9. Clones inserted in both directions were taken from this transfected phage, and a deletion body was prepared from both the clones with DNase 1. The nucleotide sequence was determined by the dideoxy method from both directions.

It was confirmed by the nucleotide sequencing that all regions coding for the API mature protein were included on this fragment. However, although the API was a secretory protein, no signal sequence and no SD sequence ahead of several Mets were identified. From this fact, the possibility of an in frame cleavage with SalI was considered.

[C] Cloning of 5'-Region of API Gene and Determination of Its Nucleotide Sequence (4) Cloning of 15-Kbp Fragment of API Gene For the purpose of cloning the whole API gene, genomic DNA isolated from *Achromobacter lyticus* M497-1 was digested with BamHI, and Southern hybridization was carried out. 2.5-Kbp SalI-digested fragments of pAPC250 obtained in (3) were labeled by nick translation using [α-³²P]dCTP, and used as a probe. A region corresponding to a 15-Kbp band detected using autoradiography and was cut out from a gel similarly electrophoresed. The DNA fragments were recovered. These fragments were inserted into pACYC184, and colony hybridization was performed using the same probe and about 1,000 transformants as a library. One positive clone was obtained (pAPW150). A plasmid was prepared therefrom, and digested with BamHI. It was confirmed by Southern hybridization of the same probe to be the desired about 15-Kbp fragment, and the 15-Kbp fragment was collected (5) Subcloning of the 600-bp EcoRI Fragment from 15-Kbp BamHI Fragment In order to obtain a DNA fragment having a region following to the 2.5-Kbp SalI fragment obtained in (3), a DNA fragment for a probe was prepared from the 2.5-Kbp fragment Since one EcoRI site had been observed in the 2.5-Kbp fragment by sequence analysis, pAPC250 was digested with SalI/EcoRI to obtain two fragments, of which a 100-bp EcoRI/SalI fragment extending to the N terminal side of the protein was collected. Then, the 5'-terminal phosphate residue of this fragment was removed with Bacterial Alkaline Phosphatase, and the resulting fragment was labeled with [γ-$^{32}$P]ATP as with the oligonucleotide. The labeled fragment was used as a probe.

20 μg of the 15-Kbp BamHI fragments were digested with EcoRI, and Southern hybridization was carried out. In this case, washing with a solution of 0.1×SSC and 0.1% SDS was performed at about 50° C.

A band prepared at the position of about 600 bp on an autoradiogram. A band corresponding to this position was cut out and eluted from a gel obtained by subjecting the EcoRI digestion of the 15-Kbp fragments to 6% polyacrylamide electrophoresis, and inserted into M13 phage mp9. Clones were obtained having inserts in both directions, and the nucleotide sequence was determined. As a result, the sequence of the 100-bp EcoRI-SalI fragment used as a probe was also confirmed. Thereafter, this 600-bp EcoRI fragment was transferred in pUC9 (pAPN600).

EXAMPLE 2 (REFER TO FIG. 3)

Figure 3:
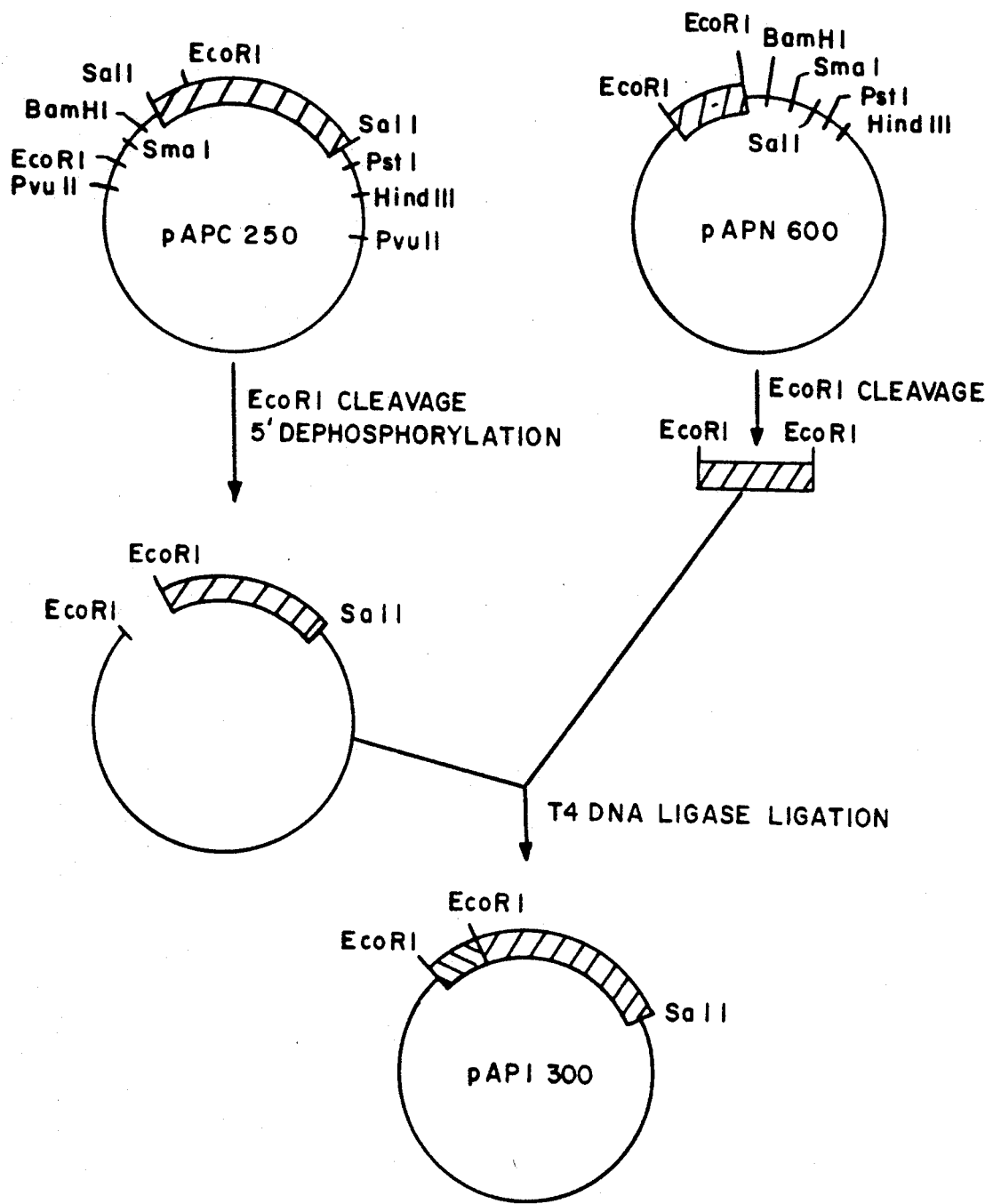
FIG. 3 shows the scheme of the construction of the whole T-API gene.
Figure 4:
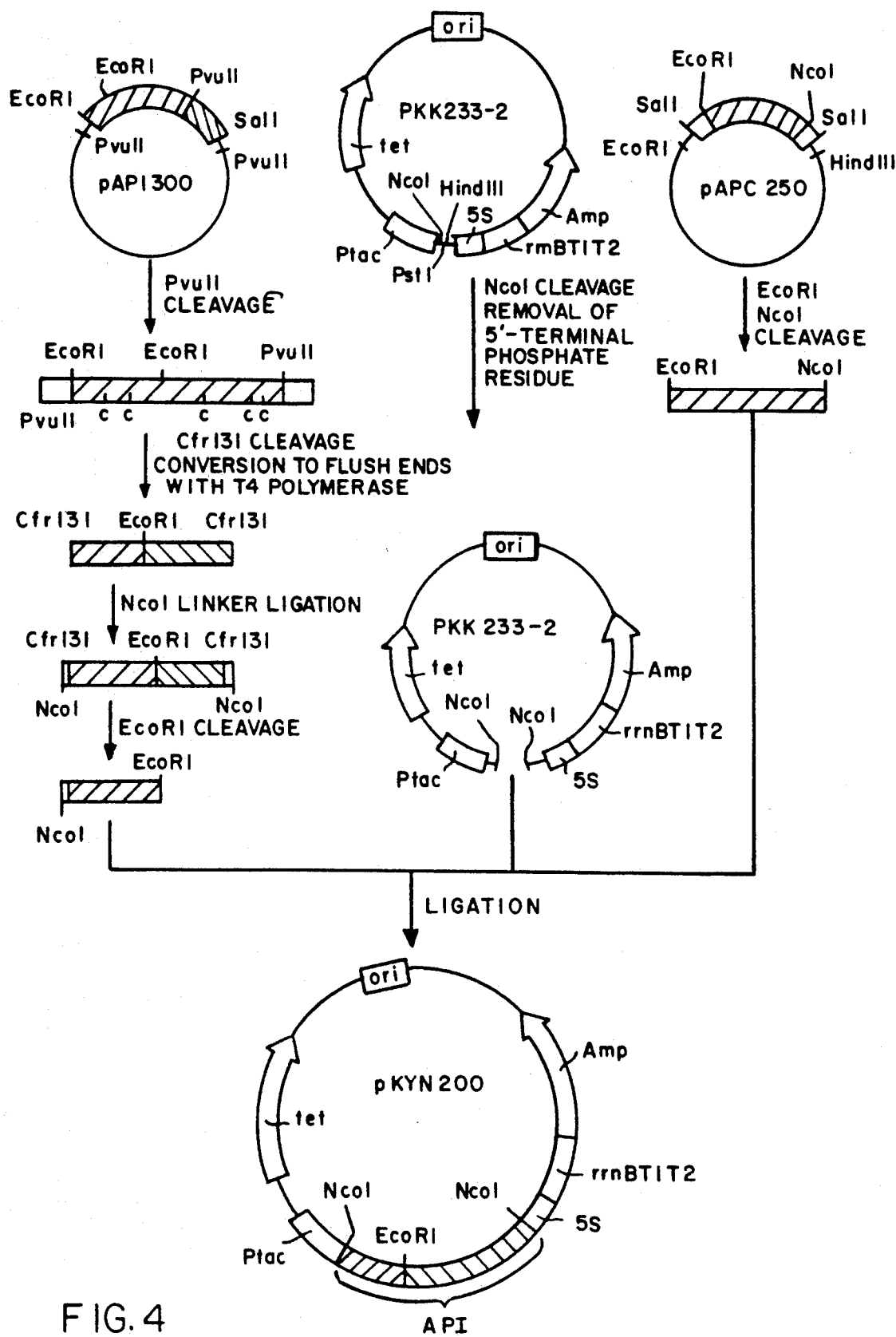
FIG. 4 is the scheme of the construction of an expression system of the T-API gene.

[D] Construction of whole API Gene (6) Construction of Plasmid Having Complete API Gene A plasmid having a whole API gene was produced as shown in FIG. 3.

(i) pAPC250 was cleaved with EcoRI, and a region positioned between the EcoRI site on the plasmid on the EcoRI site in the inserted DNA fragment was eliminated, followed by removal of the 5'-terminal phosphate residue with a bacterial alkaline phosphatase.

(ii) pAPB600 was cleaved with EcoRI, and the EcoRI inserted fragment was isolated and collected.

The fragment obtained in (i) and the fragment obtained in (ii) were ligated with each other, and thereby the plasmid having the whole API region was constructed. The direction in which the EcoRI fragment was inserted was confirmed by the size of a fragment digested, using PvuII and SalI.

EXAMPLE 3 (REFER TO FIG. 4)

[D] Construction of API Gene Expression System pAPI300 was digested with PvuII, and an about 1.7-Kbp fragment was collected from 0.8% agarose gel. Then, this fragment was digested with Cfr13I, and the ends of each of the digested fragments of the mixture were converted to flush ends with T4 DNA polymerase. The mixture was separated by 6% polyacrylamide gel electrophoresis, and an about 600-bp DNA fragment was isolated. This fragment was ligated with an 8-mer NcoI linker GCCATGGC, and then digested with EcoRI and NcoI to obtain the desired 279-bp NcoI-EcoRI fragment (i) from 6% polyacrylamide gel electrophoresis.

pAPC250 was digested with EcoRI/NcoI, and about 1.89-Kbp EcoRI NcoI fragment (ii) was collected from 0.8% agarose gel.

Expression vector pKK233-2 was digested with NcoI, and the 5'-terminal phosphate residue was removed with a bacterial alkaline phosphatase.

Fragments (i) and (ii) and pKK233-2 were ligated with one another to obtain API expression plasmid pKYN200. The direction in which an NcoI fragment was inserted was confirmed by the size of fragments which appeared by digestion with EcoRI (one site on the vector side and one site in the inserted fragment) and HindIII (one site on the vector side).

Figure 5:
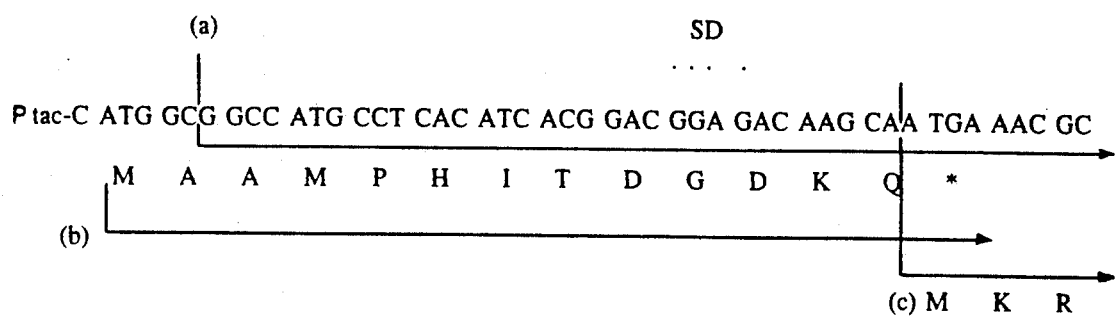
FIG. 5 is a representation showing the outline of the system for T-API expression.

This expression system is as shown in FIG. 5.

Referring to FIG. 5, the symbol (a) shows the Achromobacter-derived gene, and the translation starting from Met at the position denoted by the symbol (b) terminates at the position indicated by an arrow. The translation which has once terminated is reinitiated by using SD in the Achromobacter-derived gene from Met at the position denoted by the symbol (c), thereby producing the API protein.

EXAMPLE 4

[F] Expression of API Gene in *E. coli* UT481 and Purification of Its Product

*Escherichia coli* belongs to a lon⁻ strain (Lon=-protease La: ATP-dependent protease) It was therefore considered that the degradation of the product would be inhibited to some extent.

A transformant *Escherichia coli* UT481 transformed with pKYN200 was pre-cultivated in a medium containing 100 μg/ml of ampicillin overnight. Then, 2.5 ml of the pre-culture was added to 250 ml of the same medium and cultivated at 25° C. for 24 hours. A periplasmic protein was extracted from cells collected from the culture, by the osmotic shock procedure [G. R. Willsky et al., *J. Bacteriol.* 127:595-609 (1976)]. This protein solution was allowed to be adsorbed by QAE Spehadex A-50 (1×40 cm) equilibrate with 10 mM Tris-HCl (pH 9.5), and then eluted with linear gradient NaCl up to 500 mM. A peak eluted at 60 to 65 mM was separately taken, and dialyzed against 10 mM Tris-Hcl (pH 8.0), followed by lyophilization. The lyophilized crude protein was dissolved in 2 ml of water, and finally purified by gel filtration by HPLC using a TSK gel 2000 SW column. The conditions of HPLC were as follows:

Flow rate: 9.7 ml/minute., Buffer 0.2 M ammonium acetate;

pH 7.0

API (corresponding to the amino acid sequence extending from position 1 to position 448 shown in FIG. 1) was produced in an amount of 1.6 mg per 1 liter of culture solution, and about 0.5 mg of purified sample was obtained according to the above method. This sample showed a specific activity of 60% relative to that of the mature API (corresponding to the amino acid sequence extending from position 1 to position 268 shown in FIG. 1), and the analysis of a digest of *Vibro parahaemolyticus*-derived hemolysin revealed that this sample specifically hydrolyzed Lys—X bonds. Further, the sequence of the N-terminal 23 residues of the isolated API was completely identical with that of the standard APIs (commercial and natural products). The composition of amino acids agreed closely with that of a peptide chain extending from glycine at position 1 to glycine at position 448. The molecular weight was 48.000, which agreed approximately with a calculated value of 46,000.

TABLE 1

Composition of Amino Acids

| | Gene Product | Amino Acid Composition Deduced from Gene Gly$^1$-Gly$^{448}$ |
|---|---|---|
| Asp | 53.2 | 54 |
| Thr | 56.3 | 59 |
| Ser | 51.2 | 53 |
| Glu | 22.5 | 20 |
| Pro | 25.0 | 23 |
| Gly | 51.2 | 55 |
| Ala | 45.8 | 45 |
| Val | 26.0 | 26 |
| Met | 3.4 | 3 |
| Ile | 15.5 | 16 |
| Leu | 19.1 | 19 |
| Tyr | 13.5 | 14 |
| Phe | 13.1 | 14 |
| Lys | 10.5 | 10 |
| His | 8.0 | 9 |
| Arg | 15.4 | 16 |

What is claimed is:

1. An isolated DNA segment encoding *Achromobacter lyticus* protease I.

2. An isolated DNA sequence in accordance with claim 1, wherein said DNA segment is represented by a nucleotide sequence extending from position 387 to position 2348 shown in FIG. 1.

3. An isolated DNA sequence in accordance with claim 1 or 2, wherein said DNA segment is derived from a chromosomal segment of *Achromobacter lyticus* M497-1.

4. A recombinant DNA expression vector containing the DNA sequence of claim 1.

5. A recombinant DNA expression vector in accordance with claim 4, wherein said DNA sequence is represented by a nucleotide sequence extending from position 354 to position 2414 shown in FIG. 1.

6. A prokaryotic transformant bearing the recombinant DNA in accordance with claim 4 or 5.

7. A transformant in accordance with claim 6, wherein a host cell of said transformant is *Escherichia coli*.

8. A process for producing Achromobacter protease I which comprises cultivating the transformant in accordance with claim 6 or 7, accumulating the protease in a culture product, and recovering the same.

9. An isolated DNA sequence in accordance with claim 1, wherein said DNA segment is represented by a nucleotide sequence extending from position 1002 to position 1805 shown in FIG. 1.

10. An isolated DNA sequence in accordance with claim 1, wherein said DNA segment is represented by a nucleotide sequence extending from position 1002 to position 1808 or up to position 2348 shown in FIG. 1.

* * * * *